United States Patent [19]
Lynch, Jr. et al.

[11] Patent Number: 5,969,017
[45] Date of Patent: Oct. 19, 1999

[54] METHODS OF TREATING OR PREVENTING CARDIAC ARRHYTHMIA

[75] Inventors: Joseph J. Lynch, Jr.; Richard J. Swanson; Joseph J. Salata, all of Lansdale; Bernard Fermini, North Wales, all of Pa.

[73] Assignee: Merck & Co., Inc., Rahway, N.J.

[21] Appl. No.: 08/958,958

[22] Filed: Oct. 28, 1997

Related U.S. Application Data

[60] Provisional application No. 60/029,352, Oct. 31, 1996.

[51] Int. Cl.$^6$ .............................. C08J 5/52; C08K 5/51; A01N 57/34; A01N 57/18
[52] U.S. Cl. ......................... 524/129; 514/139; 514/140; 514/141; 514/142
[58] Field of Search ................................ 260/340.5, 378; 514/247, 129, 131, 139, 140, 141, 142; 524/129

[56] References Cited

U.S. PATENT DOCUMENTS

| | | |
|---|---|---|
| 4,963,549 | 10/1990 | Rothaul et al. . |
| 5,428,031 | 6/1995 | Sanguinetti et al. . |
| 5,506,228 | 4/1996 | Norton et al. . |
| 5,670,504 | 9/1997 | Bochis et al. . |

FOREIGN PATENT DOCUMENTS

310313 A2  4/1989  European Pat. Off. .

OTHER PUBLICATIONS

Sanguinetti, M.C., et al., Journal of General Physiology, vol. 96, pp. 195–215, 1990.
Fedida, D., et al., Circulation Research, vol. 73(1), pp. 210–216, 1993.
Spinelli, W., et al., Circulation Research, vol. 65(6), pp. 1565–1579, 1989.
Frame, L.H., et al., Circulation Research, vol. 58(4), pp. 495–511, 1986.
Snyders, D.J., et al., J. Gen. Physiol., vol. 101, pp. 513–543, 1993.
Li et al., Adrenergic modulation of ultrarapid delayed rectifier K+ . . . , Circulation Research, vol. 78(5), pp. 903–915, 1996.
Li et al., Evidence for two components of delayed rectifier K+ . . . , Circulation Research, vol. 78(4), pp. 689–696, 1996.

*Primary Examiner*—Keith D. MacMillan
*Assistant Examiner*—Vickie Kim
*Attorney, Agent, or Firm*—Valerie J. Camara; Mark R. Daniel

[57] ABSTRACT

This application discloses a method of treating or preventing atrial arrhythmias which utilizes compounds which are blockers of the ultra-rapidly-activating delayed rectifier K$^+$ current ($I_{Kur}$) of the human atrium in a use-dependent and/or rate dependent manner, and which provide the selective block preferentially at fast heart rates so that the effect is realized or maximized when required.

25 Claims, No Drawings

METHODS OF TREATING OR PREVENTING CARDIAC ARRHYTHMIA

This application claims benefit of provisional application 60/029,352, filed Oct. 31, 1996.

BACKGROUND OF THE INVENTION

This application discloses a method of treating or preventing atrial arrhythmias which utilizes compounds which are blockers of the ultra-rapidly-activating delayed rectifier $K^+$ current ($I_{Kur}$) of the human atrium in a use-dependent and/or rate-dependent manner, and which preferentially block at fast heart rates so that the effect is realized or maximized when required.

Atrial flutter and/or atrial fibrillation (AF) are the most commonly sustained cardiac arrhythmias in clinical practice and are likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Although various antiarrythmic agents are now available on the market, those having both satisfactory efficacy and a high margin of safety have not been obtained. For example, antiarrhythmic agents of Class I, according to the classification scheme of Vaughan-Williams ("Classification of antiarrhythmic drugs", *Cardiac Arrhythmias*, edited by: E. Sandoe, E. Flensted-Jensen, K. Olesen; Sweden, Astra, Sodertalje, pp 449–472, 1981) which cause a selective inhibition of the maximum velocity of the upstroke of the action potential ($V_{max}$) are inadequate for preventing ventricular fibrillation. In addition, they have problems regarding safety, namely, they cause a depression of myocardial contractility and have a tendency to induce arrhythmias due to an inhibition of impulse conduction. β-adrenergic receptor blockers and calcium channel ($I_{Ca}$) antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs that cause a selective prolongation of the action potential duration (APD) without a significant depression of the maximum upstroke velocity ($V_{max}$). Available drugs in this class are limited in number. Examples such as sotalol and amiodarone have been shown to possess interesting Class III properties (Singh B. N., Vaughan Williams E. M., "A third class of anti-arrhythmic action: effects on atrial and ventricular intracellular potentials and other pharmacological actions on cardiac muscle of MJ 1999 and AH 3747", *Br. J. Pharmacol* 1970; 39:675–689, and Singh B. N., Vaughan Williams E. M., "The effect of amiodarone, a new anti-anginal drug, on cardiac muscle", *Br. J. Pharmacol* 1970; 39:657–667), but these are not selective Class III agents. Sotalol also possesses Class II (β-adrenergic blocking) effects which may cause cardiac depression and is contraindicated in certain susceptible patients. Amiodarone also is not a selective Class III antiarrhythmic agent because it possesses multiple electrophysiological actions and is severely limited by side effects (Nademanee, K., "The Amiodarone Odessey", *J. Am. Coll. Cardiol.* 1992; 20:1063–1065.) Drugs of this class are expected to be effective in preventing ventricular fibrillation. Selective Class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration (APD). Theoretically, prolongation of the cardiac action potential can be achieved by enhancing inward currents (i.e. $Na^+$ or $Ca^{2+}$ currents; hereinafter $I_{Na}$ and $I_{Ca}$, respectively) or by reducing outward repolarizing potassium $K^+$ currents. The delayed rectifier ($I_K$) $K^+$ current is the main outward current involved in the overall repolarization process during the action potential plateau, whereas the transient outward ($I_{to}$) and inward rectifier ($I_{K1}$) $K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating). (Sanguinetti and Jurkiewicz, "Two components of cardiac delayed rectifier K+ current. Differential sensitivity to block by Class III antiarrhythmic agents", *J Gen Physiol* 1990, 96:195–215).

Class III antiarrhythmic agents currently in development, including d-sotalol, dofetilide (UK-68,798), almokalant (H234/09), E-4031 and methanesulfonamide—N—[1'-6-cyano-1,2,3,4-tetrahydro-2-naphthalenyl)-3,4-dihydro-4-hydroxyspiro[2H-1-benzopyran-2,4'-piperidin]-6yl], (+)-, monochloride (MK-499) predominantly, if not exclusively, block $I_{Kr}$. Although, amiodarone is a blocker of $I_{Ks}$ (Balser J. R. Bennett, P. B., Hondeghem, L. M. and Roden, D. M. "Suppression of time-dependent outward current in guinea pig ventricular myocytes: Actions of quinidine and amiodarone", *Circ. Res.* 1991, 69:519–529), it also blocks $I_{Na}$ and $I_{Ca}$, effects thyroid function, is as a nonspecific adrenergic blocker, and acts as an inhibitor of the enzyme phospholipase (Nademanee, K. "The Amiodarone Odessey". *J. Am. Coll. Cardiol.* 1992; 20:1063–1065). Therefore, its method of treating arrhythmia is uncertain.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging APD, prevents and/or terminates reentrant arrhythmias. Most selective, Class III antiarrhythmic agents currently in development, such as d-sotalol and dofetilide predominantly, if not exclusively, block $I_{Kr}$, the rapidly activating component of $I_K$ found both in atrium and ventricle in man.

Since these $I_{Kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de pointes, a specific type of polymorphic ventricular tachycardia which is commonly associated with excessive prolongation of the electrocardigraphic QT interval, hence termed "acquired long QT syndrome", has been observed when these compounds are utilized (Roden, D. M. "Current Status of Class III Antiarrhythmic Drug Therapy", Am J. Cardiol, 1993; 72:44B–49B). This exaggerated effect at slow heart rates has been termed "reverse frequency-dependence" and is in contrast to frequency-independent or frequency-dependent actions. (Hondeghem, L. M., "Development of Class III Antiarrhythmic Agents", J. Cardiovasc. Cardiol. 20 (Suppl. 2):S17–S22).

The slowly activating component of the delayed rectifier ($I_{Ks}$) potentially overcomes some of the limitations of $I_{Kr}$ blockers associated with ventricular arrhythmias. Because of its slow activation kinetics however, the role of $I_{Ks}$ in atrial repolarization may be limited due to the relatively short APD of the atrium. Consequently, although $I_{Ks}$ blockers may provide distinct advantage in the case of ventricular arrhythmias, their ability to affect supra-ventricular tachyarrhythmias (SVT) is considered to be minimal.

Another major defect or limitation of most currently available Class III antiarrhythmic agents is that their effect increases or becomes more manifest at or during bradycardia or slow heart rates, and this contributes to their potential for proarrhythmia. On the other hand, during tachycardia or the conditions for which these agents or drugs are intended and most needed, they lose most of their effect. This loss or diminishment of effect at fast heart rates has been termed "reverse use-dependence" (Hondeghem and Snyders, "Class III antiarrhythmic agents have a lot of potential but a long way to go: Reduced effectiveness and dangers of reverse use dependence", Circulation (1990),81:686–690; Sadanaga et al ., "Clinical evaluation of the use-dependent QRS prolongation and the reverse use-dependent QT prolongation of class III antiarrhythmic agents and their value in predicting efficacy" Amer Heart Journal (1993)126: 114–121), or "reverse rate-dependence" (Bretano, "Rate dependence of class III actions in the heart", Fundam Clin Pharmacol (1993) 7:51–59; Jurkiewicz and Sanguinetti, "Rate-dependent prolongation of cardiac action potentials by a methanesulfonanilide class III antiarrhythmic agent: Specific block of rapidly activating delayed rectifier K+current by dofetilide", Circ Res (1993) 72:75–83). Thus, an agent that has a use-dependent or rate-dependent profile, opposite that possessed by most current class III antiarrhythmic agents, should provide not only improved safety but also enhanced efficacy.

In intact human atrial myocytes, an ultra-rapidly activating delayed rectifier K+ current, ($I_{Kur}$), which is also known as the sustained outward current, $I_{sus}$ or $I_{so}$, has been identified. This current has properties and kinetics identical to those expressed by the human K+ channel clone (hKv1.5, HK2) when isolated from the human heart and stably expressed in human (HEK-293) cell lines. (Wang et al., "Sustained depolarization-induced outward current in human atrial myocytes. Evidence for a novel delayed rectifier K+ current similar to Kv1.5 cloned channel currents", Circ. Res. 1993; 73:1061–1076; Fedida et al., "Identity of a novel delayed rectifier current from human heart with a cloned K+ channel current", Circ. Res. 1993, 73:210–216; Snyders et al., "A rapidly activating and slowly inactivating potassium channel cloned from human heart. Functional analysis after stable mammalian cell culture expression", J. Gen. Physiol. 1993,101:513–543) and originally cloned from rat brain (Swanson et al., "Cloning and Expression of cDNA and genomic clones encoding three delayed rectifier potassium channels in rat brain", Neuron 1990, 4:929–939).

The ultra-rapidly activating delayed rectifier K+ current ($I_{Kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $I_{Kur}$ but has little or no effect on the other K+ channels of the heart, would overcome the short-comings and disadvantages of other currently used or developed agents. By retarding repolarization and prolonging refractoriness selectively in the human atrium without causing the delays in ventricular repolarization, a selective $I_{Kur}$ blocker would not produce arrhythmogenic after depolarizations and acquired long QT syndrome observed during treatment with current Class III drugs.

The method of treatment of atrial arrhythmia presented herein provides for greater safety and efficacy as well preferentially providing treatment at fast heart rates when treatment of this type is most desired through "use-dependent" and/or "rate-dependent" block of $I_{Kur}$.

SUMMARY OF THE INVENTION

A method of treating or preventing supraventricular tachyarrhythmias is disclosed which comprises the use of a compound which blocks the ultra-rapidly-activating delayed rectifier K+ current ($I_{Kur}$) of the human atrium in a use-dependent and/or rate-dependent manner, and which preferentially blocks at fast heart rates so that the effects are primarily realized or maximized when required.

Additionally, it has been found that compounds which block the ultra-rapidly-activating delayed rectifier K+ current ($I_{Kur}$) of the human atrium in a use-dependent and/or rate-dependent manner, and with a selectivity ratio at least about 10 times the block of the rapidly-activating delayed rectifier K+ current ($I_{Kr}$), the slowly-activating delayed rectifier K+ current ($I_{Ks}$) or the inward rectifier K+ current, $I_{K1}$, preferentially or selectively prolong the atrial vs. the ventricular refractory period.

Specifically, a method of treating or preventing cardiac arrhythmia in mammals is presented which comprises block of the ultra-rapidly-activating delayed rectifier K+ current ($I_{Kur}$) by a compound which exhibits use-dependent and/or rate-dependent block at a concentration of about 1 $\mu$M or less.

More specifically, a method of treating or preventing cardiac arrhythmia in mammals is presented which comprises block of the ultra-rapidly-activating delayed rectifier K current ($I_{Kur}$) by a compound which exhibits use-dependent and/or rate-dependent block at a concentration of about 1 $\mu$M or less, and the concentration which blocks $I_{Kur}$ by 50% ($IC_{50}$) is at least about 10 fold lower than the concentration which blocks the slowly activating delayed rectifier potassium K+ current ($I_{Ks}$), the rapidly activating and deactivating delayed rectifier potassium current ($I_{Kr}$) or the inward rectifier + current, $I_{K1}$.

Among the compounds which exemplify these methods of treatment or prevention are pyridazinones and phosphine oxides and their derivatives which exhibit use-dependent and/or rate-dependent block and which selectively block the ultra-rapidly-activating delayed rectifier K+ current ($I_{Kur}$) of the human atrium with greater selectivity over the rapidly-activating delayed rectifier K+ current ($I_{Kr}$), the slowly-activating delayed rectifier K+ current ($I_{Ks}$) or the inward rectifier K+ current, $I_{K1}$ and are therefore effective in the treatment of cardiac arrhythmia.

DETAILED DESCRIPTION OF THE INVENTION

A method of treating or preventing supraventricular tachyarrhythmias is disclosed which comprises the use of a compound which exhibits use-dependent and/or rate-dependent block of the ultra-rapidly-activating delayed rectifier K$^+$ current ($I_{Kur}$) of the human atrium at a concentration of about 1 μM or less.

More specifically, a method of treating or preventing supraventricular tachyarrhythmias is disclosed which comprises the use of a compound which exhibits use-dependent and/or rate-dependent block and which selectively blocks the ultra-rapidly-activating delayed rectifier K$^+$ current ($I_{Kur}$) at a concentration of about 1 μM or less and the concentration which blocks $I_{Kur}$ by 50% ($IC_{50}$) is at least about 10 fold lower than the concentration which blocks the slowly activating delayed rectifier potassium K$^+$ current ($I_{Ks}$), the rapidly activating and deactivating delayed rectifier potassium current ($I_{Kr}$) or the inward rectifier K$^+$ current $I_{K1}$.

Additionally a method of treating or preventing cardiac arrhythmia in mammals is presented which comprises the use of a compound which exhibits use-dependent and/or rate-dependent block of the ultra-rapidly-activating delayed rectifier K$^+$ current ($I_{Kur}$) of the human atrium at a concentration of about 1 μM or less.

More specifically, a method of treating or preventing cardiac arrhythmia in mammals is presented which comprises block of the ultra-rapidly-activating delayed rectifier K$^+$ current ($I_{Kur}$) by a compound which exhibits use-dependent and/or rate-dependent block at a concentration of about 1 μM or less and the concentration which blocks $I_{Kur}$ by 50% ($IC_{50}$) is at least about 10 fold lower than the concentration which blocks the slowly activating delayed rectifier potassium K$^+$ current ($I_{Ks}$), the rapidly activating and deactivating delayed rectifier potassium current ($I_{Kr}$) or the inward rectifier K+ current, $I_{K1}$.

By "block of the ultra-rapidly-activating delayed rectifier K$^+$ current ($I_{Kur}$)" is meant a reduction of the time-dependent net outward current as measured in an isolated human atrial myocyte using the conditions defined below in the "Voltage claim Measurement of Ionic Currents In Vitro", Section B.

By "selective block of $I_{Kur}$" is meant, compounds which block the $I_{Kur}$ current measured in isolated human atrial myocytes by 50% at a concentration of about 1 μM or less, defined as the $IC_{50}$, and the concentration that blocks $I_{Kur}$ by 50% is at least about 10 fold lower than the concentration required to cause 50% block of $I_{Ks}$ and/or $I_{Kr}$ and/or $I_{K1}$.

As used herein, the terms "treating" or "treatment" refer to the termination and/or reduction of the severity of the condition being targeted, i.e. supraventricular tachyarrhythmia, cardiac arrhythmia, atrial flutter, atrial arrhythmia and/or atrial fibrillation.

By "use-dependent block" is meant that block of the outward K$^+$ current increases with use, or during repetitive depolarization of a cardiac cell. Thus, "use-dependent block" of the outward K$^+$ current is block that occurs to a progessively greater extent with each successive depolarization in a train or sequence of pulses or depolarizations delivered at a given rate or frequency. For example, during a train of about 10 depolarizations at frequency of about 1 Hz, the block is "use-dependent" if the amount of block is greater for the 10th pulse than for the 1st pulse of the train. By "rate-dependent" block is meant that block of the outward K$^+$ current occurs to a greater extent or preferentially at faster rates of depolarization or heart rates. For example, during about 10 second long trains of depolarizations delivered at frequencies of about 1 and about 3 Hz, the block is "rate-dependent" if the amount of block of the current during the last pulse of the 10 sec train is greater at about 3 Hz than at about 1 Hz. A compound may exhibit both "use-dependent" and "rate-dependent" block.

Use-dependent and/or rate-dependent block are important and desirable property of a blocker of outward K+ currents that is proposed to treat atrial tachycardic arrhythmias. An ideal agent would block exclusively or preferentially at fast rates, thereby exerting its effect only when required, since block of the outward K+ current is required at rapid heart rate while block at slow or normal heart rates is unneeded and may induce unwanted side effects.

By "selectively blocks the ultra-rapidly-activating delayed rectifier K$^+$ current ($I_{Kur}$) of the human atrium with greater selectivity over the rapidly-activating delayed rectifier K$^+$ current ($I_{Kr}$), the slowly-activating delayed rectifier K$^+$ current ($I_{Ks}$) or the inward rectifier K$^+$ current, $I_{K1}$" is meant that the method of this invention relies on the ability of certain compounds to block the ultra-rapidly-activating delayed rectifier K$^+$ current ($I_{Kur}$) of the human atrium with the specificity needed to reduce side effects which result when this current and any or all of the rapidly-activating delayed rectifier K$^+$ current ($I_{Kr}$), the slowly-activating delayed rectifier K$^+$ current ($I_{Ks}$) or the inward rectifier K$^+$ current, $I_{K1}$ are blocked. That is, an advantage of this invention lies not only in superior treatment of supraventricular tachyarrhythmias but also in reduction of side effects which result from less specific or other methods of treatment.

In another embodiment of this invention, a method of treating and/or preventing atrial arrhythmia is presented which comprises the administration of a compound which provides for use-dependent and/or rate-dependent block of the ultra-rapidly-activating delayed rectifier K$^+$ current ($I_{Kur}$) at a concentration of about 1 μM or less.

In a further embodiment of this invention, a method of treating and/or preventing atrial arrhythmia is presented which comprises the administration of a compound which provides for use-dependent and/or rate-dependent block of the ultra-rapidly-activating delayed rectifier K$^+$ current ($I_{Kur}$) at a concentration of about 1 μM or less and the concentration which blocks $I_{Kur}$ by 50% ($IC_{50}$) is at least about 10 fold lower than the concentration which blocks the slowly activating delayed rectifier potassium K$^+$ current ($I_{Ks}$), the rapidly activating delayed rectifier potassium current ($I_{Kr}$) or the inward rectifier K+ current, $I_{K1}$.

In another embodiment of this invention, a method of treating and/or preventing atrial flutter or atrial fibrillation is presented which comprises the administration of a compound which provides for use-dependent and/or rate-dependent block of the ultra-rapidly-activating delayed rectifier K$^+$ current ($I_{Kur}$) at a concentration of about 1 μM or less.

In further embodiments of this invention, a method of treating and/or preventing atrial flutter or atrial fibrillation is disclosed which comprises the administration of a compound which provides for use-dependent and/or rate-dependent block of the ultra-rapidly-activating delayed rectifier K$^+$ current ($I_{Kur}$) at a concentration of about 1 μM or less and the concentration which blocks $I_{Kur}$ by 50% ($IC_{50}$) is at least about 10 fold lower than the concentration which blocks the slowly activating delayed rectifier potassium K$^+$ current ($I_{Ks}$), the rapidly activating and deactivating delayed rectifier potassium current ($I_{Kr}$) or the inward rectifier K+ current, $I_{K1}$.

Among the compounds which exemplify these methods of treatment or prevention are pyridazinones such as those illustrated by Formula I:

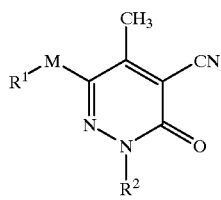

wherein:
$R^1$ and $R^2$ are selected from:
(1) aryl, wherein aryl is defined as any stable monocyclic or bicyclic carbon ring of up to 7 members in each ring, wherein at least one ring is aromatic,
(2) substituted aryl in which as many as three substituents, X, Y, and Z, may be present, wherein X, Y and Z independently are selected from:
   (a) hydrogen,
   (b) $C_{1-10}$ alkyl, unsubstituted or substituted with one or more substituents selected from:
      (i) aryl,
      (ii) substituted aryl in which the substituents are X', Y' and Z',
      (iii) heteroaryl, wherein heteroaryl is defined as any stable monocyclic or bicyclic carbon ring of up to 7 members in each ring, wherein at least one ring is aromatic and wherein from one to four carbon atoms are replaced by heteroatoms selected from the group consisting of N, O and S,
      (iv) substituted heteroaryl in which the substituents are X', Y', and Z',
      (v) unsubstituted or substituted aryloxy, in which the substituents on aryl are X', Y' and Z',
      (vi) unsubstituted or substituted heteroaryloxy, in which the substituents on aryl are X', Y' and Z',
      (vii) $C_{1-6}$ alkoxy,
      (viii) —$OCOC_{1-6}$alkyl,
      (ix) —$OCO_2C_{1-6}$alkyl,
      (x) —$NO_2$,
      (xi) —$NR^3R^4$, wherein $R^3$ and $R^4$ are independently selected from:
         (a') hydrogen,
         (b') $C_{1-6}$ alkyl unsubstituted or substituted with one or more of the substituents selected from:
            (i') aryl, which is unsubstituted or substituted with X', y' and Z',
            (ii') heteroaryl, which is unsubstituted or substituted with X', Y' and Z',
            (iii') —OH,
            (iv') —$OR^5$,
            (v') —$C_{1-6}$alkoxy,
            (vi') —$CO_2H$,
            (vii') oxo,
            (viii') —$C_{3-7}$cycloalkyl,
            (ix') —$C_{1-6}$alkyl—OH,
            (x') —$C_{1-6}$alkyl—$OR^5$,
         (c') or where $R^3$ and $R^4$ and the N to which they are attached may form an unsubstituted or substituted 3 to 7-membered heterocyclic ring which may include one or two addition heteroatoms independently selected from the consisting of O, S(O)p, $NR^6$ wherein $R^6$ is hydrogen, or $C_{1-6}$alkyl and p is 0, 1 or 2; such as morpholine, thiomorpholine, piperidine or piperizine,
      (xii) —$NR^3COC_{1-6}$alkyl—$R^4$,
      (xiii) —$NR^3CO_2C_{1-6}$alkyl—$R^4$,
      (xiv) —$NR^3CONR^3R^4$,
      (xv) —$OCONR^3R^4$,
      (xvi) —CHO,
      (xvii) —$CO_2H$,
      (xviii) —$CONR^3R^4$,
      (xix) —OH,
      (xx) —$OR^5$,
      (xxi) —$OC_{1-6}$alkylOH,
      (xxii) —$OC_{1-6}$alkyl$OR^5$,
      (xxiii) oxo,
   (c) $C_{1-6}$alkyl wherein one or more of the alkyl carbons is replaced by a group selected from —$NR^3$—, —O—, —$S(O)_p$—, —$CO_2$—, —$O_2C$—, —$CONR^3$—, —$NR^3CO$—, —$NR^3CONR^4$—, —CH(OH)—, alkenyl or alkynyl and the alkyl may be unsubstituted or substituted with one or more substituents selected from:
      (i) aryl,
      (ii) substituted aryl in which the substituents are X', Y' and Z',
      (iii) heteroaryl,
      (iv) substituted heteroaryl in which the substituents are X', Y', and Z',
      (v) unsubstituted or substituted aryloxy, in which the substituents on aryl are X', Y' and Z',
      (vi) unsubstituted or substituted heteroaryloxy, in which the substituents on aryl are X', Y' and Z',
      (vii) $C_{1-6}$ alkoxy,
      (viii) —$OCOC_{1-6}$alkyl,
      (ix) —$OCO_2C_{1-6}$alkyl,
      (x) —$NO_2$,
      (xi) —$NR^3R^4$, wherein $R^3$ and $R^4$ are defined above,
      (xii) —$NR^3COC_{1-6}$alkyl—$R^4$,
      (xiii) —$NR^3CO_2C_{1-6}$alkyl—$R^4$,
      (xiv) —$NR^3CONR^3R^4$,
      (xv) —$OCONR^3R^4$,
      (xvi) —CHO,
      (xvii) —$CO_2H$,
      (xviii) —$CONR^3R^4$,
      (xix) —OH,
      (xx) —$OR^5$,
      (xxi) —$OC_{1-6}$alkylOH,
      (xxii) —$OC_{1-6}$alkyl$OR^5$,
      (xxiii) oxo,
   (d) $C_{1-10}$alkoxy, unsubstituted or substituted with one or more substituents selected from:
      (i) aryl, (ii) substituted aryl in which the substituents are X', Y' and Z',
      (iii) heteroaryl,
      (iv) substituted heteroaryl in which the substituents are X', Y', and Z',
      (v) unsubstituted or substituted aryloxy, in which the substituents on aryl are X', Y' and Z',
      (vi) unsubstituted or substituted heteroaryloxy, in which the substituents on aryl are X', Y' and Z',
      (vii) $C_{1-6}$ alkoxy,
      (viii) —$OCOC_{1-6}$alkyl,
      (ix) —$OCO_2C_{1-6}$alkyl,
      (x) —$NO_2$,
      (xi) —$NR^3R^4$, wherein $R^3$ and $R^4$ are defined above,
      (xii) —$NR^3COC_{1-6}$alkyl—$R^4$,
      (xiii) —$NR^3CO_2C_{1-6}$alkyl—$R^4$,
      (xiv) —$NR^3CONR^3R^4$,
      (xv) —$OCONR^3R^4$, (xvi) —CHO,
(xvii) —CO$_2$H,
(xviii) —CONR$^3$R$^4$,
(xix) —OH,
(xx) —OR$^5$,
(xxi) —OC$_{1-6}$alkylOH,
(xxii) —OC$_{1-6}$alkylOR$^5$,
(xxiii) oxo, (e) C$_{1-10}$alkyl wherein one or more of the alkyl carbons is replaced by a group selected from —NR$^3$—, —O—, —S(O)$_p$—, —CO$_2$—, —O$_2$C—, —CONR$^3$—, —NR$^3$CO—, —NR$^3$CONR$^4$—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y' and Z',
(v) unsubstituted or substituted aryloxy, in which the substituents on aryl are X', Y' and Z',
(vi) unsubstituted or substituted heteroaryloxy, in which the substituents on aryl are X', Y' and Z',
(vii) C$_{1-6}$ alkoxy,
(viii) —OCOC$_{1-6}$alkyl,
(ix) —OCO$_2$C$_{1-6}$alkyl,
(x) —NO$_2$,
(xi) —NR$^3$R$^4$, wherein R$^3$ and R$^4$ are defined above,
(xii) —NR$^3$COC$_{1-6}$alkyl—R$^4$,
(xiii) —NR$^3$CO$_2$C$_{1-6}$alkyl—R$^4$,
(xiv) —NR$^3$CONR$^3$R$^4$,
(xv) —OCONR$^3$R$^4$,
(xvi) —CHO,
(xvii) —CO$_2$H,
(xviii) —CONR$^3$R$^4$,
(xix) —OH,
(xx) —OR$^5$,
(xxi) —OC$_{1-6}$alkylOH,
(xii) —OC$_{1-6}$alkylOR$^5$,
(xxiii) oxo, (f) aryl,
(g) substituted aryl wherein the substituents are X', Y' or Z',
(h) aryloxy,
(i) substituted aryloxy wherein the substituents are X', Y' or Z',
(j) halogen,
(k) —NO$_2$,
(l) —NR$^3$R$^4$ wherein R$^3$ and R$^4$ are defined above,
(m) —NR$^3$COC$_{1-6}$alkyl—R$^4$,
(n) —NR$^3$CO$_2$C$_{1-6}$alkyl—R$^4$,
(o) —NR$^3$CONR$^3$R$^4$,
(p) —OCONR$^3$R$^4$,
(q) —CN,
(r) —CHO,
(s) —CO$_2$H,
(t) —CONR$^3$R$^4$,
(u) —CF$_3$,
(v) —S(O)$_p$R$^7$, wherein R$^7$ is hydrogen, C$_{1-6}$alkyl, trifluoromethyl, or phenyl and p is 0, 1 or 2,
(x) —CH(OR$^8$)(OR$^9$), wherein R$^8$ and R$^9$ are C$_{1-3}$alkyl or taken together form an ethyl or propyl bridge,
(y) R$^3$C(O)n—wherein R$^3$ is defined above, and n is 1 or 2,
(z) OH,
(aΔ) OR$^5$, and
(bΔ) —R$^5$;

or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) C$_{1-6}$alkyl,
(c) C$_{2-6}$alkenyl,
(d) halogen,
(e) —NR$^3$R$^4$, wherein R$^3$, R$^4$, and m are as defined above,
(f) —CN,
(g) —CHO,
(h) —CO$_2$H,
(i) —CONR$^3$R$^4$,
(j) —CF$_3$,
(k) —S(O)$_p$R$^7$, wherein R$^7$ is hydrogen, C$_{1-6}$alkyl, trifluoromethyl, or phenyl, and p is 0, 1 or 2,
(l) —OH,
(m) —OR$^5$, and
(n) —R$^5$;

R$^5$ is selected from:
(a) —PO(OH)O$^-$M$^+$, wherein M$^+$ is a positively charged inorganic or organic counterion,
(b) —SO$_3^-$M$^+$,
(c) —CO(CH$_2$)$_q$CO$_2^-$M$^+$, wherein q is 1–3, and
(d) —CO—C$_{1-6}$alkyl—NR$^6$R$^7$, wherein R$^6$ and R$^7$ are as defined above and the alkyl is unsubstituted or substituted with one or more substituents selected from:
(i) hydroxy,
(ii) C$_{1-6}$alkoxy,
(iii) —NR$^{16}$R$^{17}$, wherein R$^{16}$ and R$^{17}$ are independently selected from:
(a') hydrogen, and
(b') C$_{1-6}$alkyl,
(iv) —COOR$^6$, wherein R$^6$ is as defined above,
(v) phenyl,
(iv) substituted phenyl in which the substituents are X, Y and Z,
(vii) heteroaryl,
(viii) —SH, and
(ix) —S—C$_{1-6}$alkyl;

M is selected from S(O)$_p$, where p is defined above; and n is 1 or 2;

or a pharmaceutically acceptable salt, hydrate or crystal form thereof.

Additional compounds which exemplify these methods are phosphine oxides such as those illustrated by Formula II:

II wherein
R$^{1a}$ is phenyl;
R$^{2a}$ is aryl;
R$^{3a}$ is selected from:
a) C$_1$–C$_6$ alkyl-aryl, where the aryl group may be unsubstituted or substituted with one to four substituents independently selected from halo and C$_1$–C$_3$ alkyl, and
b) unsubstituted or substituted benzyl, where the substituent is (C$_1$–C$_5$ alkyl)n;

n is selected from 0, 1, 2, 3 and 4;

or a pharmaceutically acceptable salt, hydrate or crystal form thereof.

Specific compounds which exemplify these methods are:

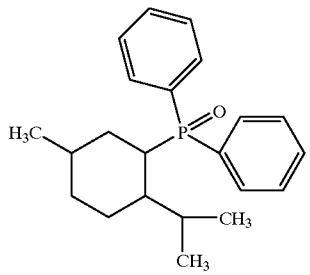

(2-Isopropyl-5-methylcyclohexyl)diphenylphosphine oxide, also referred to as Compound "A";

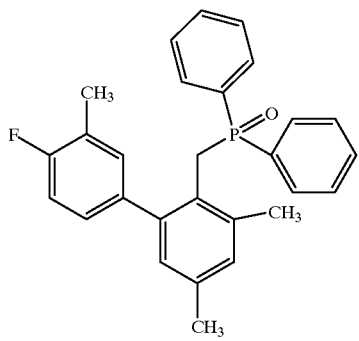

2-(Diphenylphosphinylmethyl)-4'-fluoro-3,5,3'-trimethyl-biphenyl, also referred to as Compound "B";

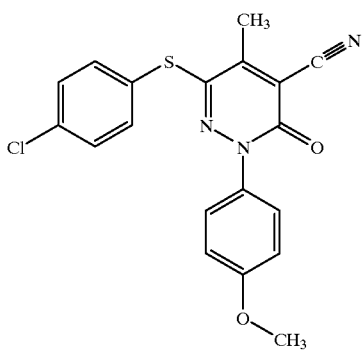

6-(4-Chlorophenylthio)-2-(4-methoxyphenyl)-5-methyl-3-oxo-2,3-dihydropyridazine-4-carbonitrile, also referred to as Compound "C"; and

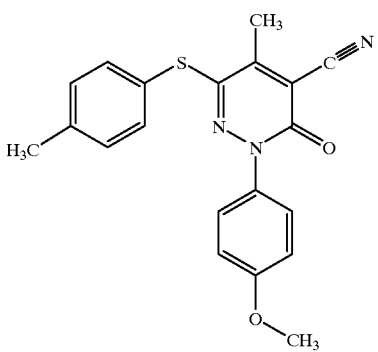

2-(4-methylphenyl)-5-methyl-3-oxo-6-(4-methylphenylthio)-2,3-dihydropyridazine-4-carbonitrile, also referred to as Compound "D";

or a pharmaceutically acceptable salt, hydrate or crystal form thereof.

The compounds of the present invention may have asymmetric centers and occur as racemates, racemic mixtures, and as individual diastereomers, with all possible isomers, including optical isomers, being included in the present invention. When any variable (e.g. aryl, n, $R^{1a}$, $R^2$, etc.) occurs more than one time in any constituent, its definition on each occurrence is independent at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl. The term "arloxy" is intended to mean an aryl group, as defined above, where the point of attachment is through an oxygen moiety.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. The term "heteroarloxy" is intended to mean a heteroaryl group, as defined above, where the point of attachment is through an oxygen moiety.

Lines drawn into the ring systems from substituents (such as from $R^2$, $R^3$, $R^4$, etc.) indicate that the indicated bond may be attached to any of the substitutable ring carbon atoms.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes A–C, in addition to other standard manipulations such as ester hydrolysis, cleavage of protecting groups, etc., as may be known in the literature or exemplified in the experimental procedures. The disclosure of U.S. Pat. Nos. 5,506,228 and 5,670,504, issued on Apr. 9, 1996 and Sep. 23, 1997, respectively, are hereby incorporated by reference.

These reactions may be employed in a linear sequence to provide the compounds of the invention or they may be used to synthesize fragments which are subsequently joined by the alkylation reactions described in the Schemes.

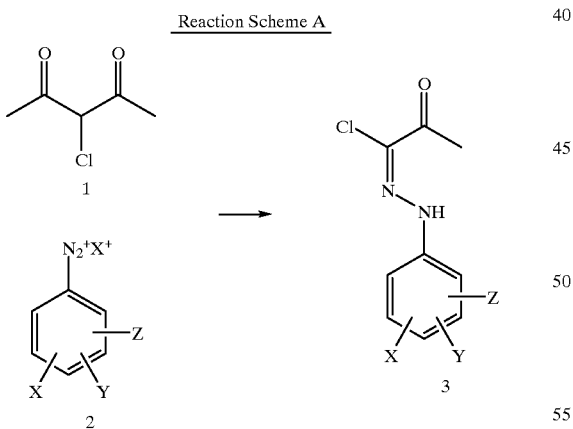

Reaction Scheme A

Reaction of commercially available 3-chloropentane-2,4-dione (1) with aryldiazonium salts (2) in the presence of a base such as aqueous sodium acetate gives chloroacetylhydrozone derivatives (3) with loss of acetic acid via an $S_E1$ type mechanism [*Org. Reactions* 10, 1–142 (1959); *J. Am. Chem. Soc.*, 84, 143–178 (1979)]. The diazonium salts can be conveniently prepared by reacting arylamines with sodium nitrite in acid such as hydrochloric acid or directly with nitrosyl chloride [*J. Org. Chem.*, 26, 5149, 2053 (1961); *Org. Syn.*, 43, 12 (1963)]

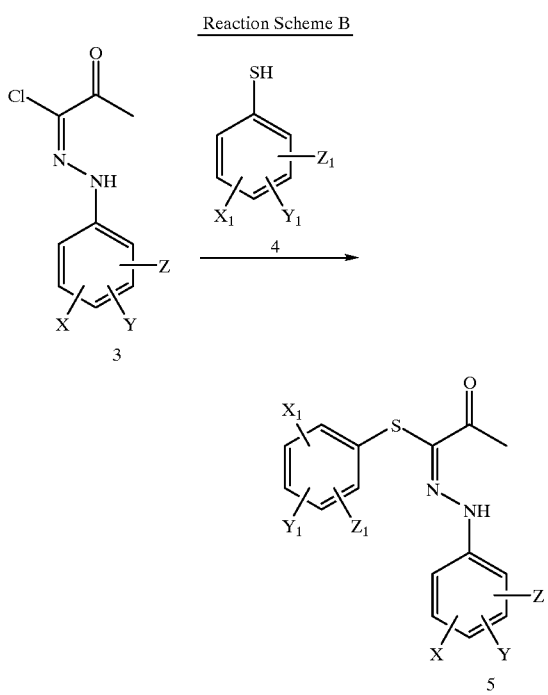

Reaction Scheme B

Reaction of chloroacetylhydrazone (3) with arylmercaptan (4) in the presence of a base such as triethylamine in a solvent such as DMF gives thioether (5). Alternatively, the sodium salt of the mercaptan can be prepared and added to (3) as referenced in *Polish J. Chemistry* 64, 741(1990).

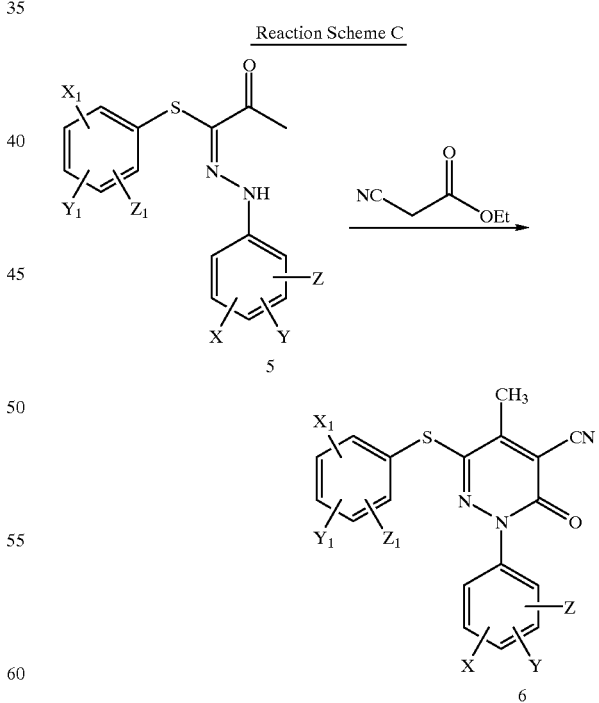

Reaction Scheme C

Reaction of compound (5) with ethylcyanoacetate under Knoevenagel conditions with ammonnium acetate produces pyridazinone analogs (6). The type of aromatic substitution may require forcing conditions at high temperatures to achieve successful cyclization.

Current therapy aimed at treating or preventing supraventricular arrhythmias and maintaining sinus rhythm is fraught with a variety of problems including incomplete or poor efficacy, coincident ventricular effects including proarrhythmia, increased mortality and noncardiac side effects. Some of the more dangerous proarrhythmic and other side effects appear to be related to the sodium channel blocking properties of many of the currently utilized anti-arrhythmic agents. Other newer agents that selectively block the delayed rectifier K$^+$ current, $I_K$ (either $I_{Kr}$ or $I_{Ks}$ or both) are undergoing investigation but these agents do not selectively affect atrial refractoriness, rather they affect the ventricle as well, thereby retaining a potential for ventricular proarrhythmia while being administered to treat atrial arrhythmias. It has now been found that compounds, which at a concentration of about 1 μM or less, selectively block 50% ($IC_{50}$) of the $I_{Kur}$ current measured in isolated myocytes and exhibit a selectivity ratio at least about 10 over block of $I_{Ks}$, $I_{Kr}$ and $I_{K1}$, results in treatment which provides for prolonged refractoriness by retarding repolarization in the atrium without causing the delays in ventricular repolarization that underlie arrhythmogenic afterdepolarizations and long QT syndrome observed during treatment with current Class III drugs.

The specificity and utility of the exemplified compound as anti-arrhythmic agent is shown by the following voltage-clamp studies in CHO cells expressing human Kv1.5 and in isolated human atrial myocytes and guinea pig isolated ventricular myocytes in vitro.

VOLTAGE CLAMP MEASUREMENT OF IONIC CURRENTS IN VITRO

A. Measurement of Kv1.5 in CHO cells
Expression of Kv1.5 in CHO Cells

A cDNA encoding Kv1.5, isolated from a human fetal heart library, was subcloned into pcDNAI/Neo (Invitrogen) as a Hind III—Xba I fragment.

CHOKI cells were plated at 2.7×10$^4$ cells/60 mm dish and incubated at 37° C., in a 5% CO$_2$ environment for three days. Cells were then washed twice and covered with 3 ml of OptiMEM medium (Gibco). Plasmid/DOTAP solution (consisting of 5 mg of Kv1.5 in pcDNAI/Neo and 30 mg DOTAP transfection reagent (Boehringer Mannheim) in 1 ml of OptiMEM) was added dropwise to each plate while swirling. Plates were incubated overnight and the media then changed to 5 mls of F12 (Gibco) supplemented with 10% FBS (Sigma), 1,000 U/ml penicillin 1,000 mg/ml streptomycin (Gibco), and 2 mM glutamine (Gibco). After two more days, the cells were trypsinized and replated on 100 mm dishes in supplemented F12 media including 1 mg/ml G418 (Gibco). The medium was changed daily until nontransfected cells were killed. Cell lines were grown from individual clones and tested for expression of Kv1.5 using both the $^{86}$RB efflux assay and voltage clamp protocols. Lines exhibiting the highest level of expression were then recloned by serial dilution. These cells were maintained in culture and on each experimental day were freshly isolated by mild trypsinization.

Voltage Clamp Technique:

CHO cells plated on glass coverslips were placed in a 1-ml chamber mounted on the stage of an inverted microscope, and perfused at 2–3 ml/min with the following solution (in mM/L): 132 NaCl, 4 KCl, 1.2 MgCl$_2$, 10 HEPES (formal name: N-2-Hydroxyethyl piperazine-N'-2-ethanesulfonic acid), 11.1 glucose. CaCl$_2$ (0.5–1.8 mM) was present in some experiments, and had no effects on Kv1.5. Nisoldipine (0.4 mM–1.0 mM), a relatively specific blocker of L-type Ca$^{2+}$ channels was present in all experiments. The patch-clamp technique was used to record ionic currents in the whole-cell configuration. Patch pipettes were obtained using a two stage puller from square bore (1.0 mm o.d.) borosillicate capillary tubing. Pipettes were filled with the following solution (in mM/L): 110 K-Gluconate or K-Aspartate, 20 KCl, 5 MgATP, 5 EGTA, 5–10 HEPES, pH 7.2. The electrodes had tip resistances ranging from 3 to 10 Mohm when filled with this solution. Following seal formation, the membrane was ruptured by gentle suction to establish the whole-cell configuration, and negative pressure was maintained on the pipette using a 1 ml gas-tight syringe attached via air tight tubing to the suction port of the microelectrode holder. Series resistance was compensated 70–85%. Currents were sampled at 5 kHz using an Axopatch 200 A amplifier (Axon Instruments) or a List EPC-7 clamp amplifier (List Electronic) and were low pass filtered at 1 kHz. Data acquisition and analysis were perform ed using pClamp soft ware (Axon Instruments) and an IBM compatible 486 computer.

Measurements of Kv1.5 Expressed Currents:

Kv1.5 currents were elicited by 150 ms depolarizing test pulses to +40 mV from a holding potential of −80 mV. The effects of test agents were assessed at steady-state. Data was analyzed as % block from control current amplitude. The amplitude of Kv1.5 was measured as the amplitude of the time-dependent net outward current at the end of the test pulse, relative to the holding current level. $IC_{50}$ for rested state and use-dependent block were determined from the first and tenth pulses, respectively, during a series of 10 consecutive pulses delivered at 1 Hz. All experiments were performed at room temperature (22–24° C.).

B. Measurement of $I_{Kur}$ in Human Atrial Myocytes
Isolation of Human Atrial Myocytes:

Human myocytes were isolated from specimens of right atrial appendage obtained from patients undergoing cardiopulmonary bypass, using a modification of the procedure described by Fermini B, Wang Z, Duan D and Nattel S., "Differences in rate dependence of transient outward current in rabbit and human atrium" *Am. J. Physiol.* 263:H1747–H1754 (1992). All tissues were collected in accordance with Temple University School of Medicine Institutional guidelines. All atrial specimens were grossly normal at the time of excision. Tissue samples were quickly immersed in cold (0–4° C.) cardioplegia solution containing (in mM/L): 50 KH$_2$PO$_4$, 8 MgSO$_4$, 10 NaHCO$_3$, 5 adenosine, 25 taurine, 140 glucose, and 100 mannitol, pH 7.4 and bubbled with 100% O$_2$. Specimens were minced into 0.5–1 mm cubes and transferred to a 50-ml conical tube containing an ultra low calcium wash solution containing (in mM/L): 137 NaCl, 5 KH$_2$PO$_4$, 1 MgSO$_4$, 10 taurine, 10 glucose, 5 HEPES and 0.1 EGTA (formal name: Ethyleneglycol-bis-(b-aminoethyl ether) N,N,N',N'-tetraacetic acid), pH 7.4 (22–24° C.). The tissue was gently agitated by continuous bubbling with 100% O$_2$ for 5 min. The tissue was then incubated in 5 ml of solution containing (in mM/L): 137 NaCl, 5 KH$_2$PO$_4$, 1 MgSO$_4$, 10 taurine, 10 glucose, and 5 HEPES supplemented with 0.1% bovine albumin, 1.5 mg/ml collagenase CLS II (Worthington Biochemical), and 1.0 mg/ml protease type XXIV (Sigma Chemical Co.), pH 7.4 (37° C.), and bubbled continuously with 100% O$_2$. The supernatant was removed after 40 min and discarded. The chunks were then incubated in a solution of the same ionic composition but supplemented with only collagenase and 100 mM CaCl$_2$. Microscopic examination of the medium was performed every 10–20 min to determine the number and quality of isolated cells. When the yield appeared maximal, the tissue chunks were suspended in a modified Kraftbrühe solution containing (in mM/L): 25 KCl, 10 KH$_2$PO$_4$, 25 taurine, 0.5 EGTA, 22 glucose, 55 glutamic acid, and 0.1% bovine albumin, pH 7.3 (22–24° C.) and gently triturated using a large bore Pasteur pipette. The supernatant was collected in a 50 ml centrifuge tube. The cell suspension was centrifuged for 2 min at 1000 rpm and the resulting pellet was resuspended in 0.2 mM HBS solution containing (in mM/L): 132 NaCl, 4 KCl, 1.2 MgCl$_2$, 10 HEPES and 11.1 glucose, pH 7.2. Cells were used within 2–24 hr after isolation.

Voltage-clamp technique:

A small aliquot of the solution containing the isolated human atrial myocytes was placed in a 1-ml chamber mounted on the stage of an inverted microscope. Five minutes were allowed for cell adhesion to the bottom of the chamber. To record $I_{Kur}$, human atrial myocytes were superfused with a solution of the same ionic composition as that used for Kv1.5. An alternative external solution was sometimes used in which NaCl was replaced with NMDG (formal name: N-methyl-d-glucamine) to inhibit $I_{Na}$. NMDG had no effects on $I_{Kur}$ and there were no notable quantitative differences in the degree of block of $I_{Kur}$ with these two conditions.

Currents were elicited by 150 ms depolarizing test pulses to +40 mV from a holding potential of –50 mV to inactivate $I_{to}$ and $I_{Na}$. The amplitude of $I_{Kur}$ was measured as the amplitude of the time-dependent current at the end of the test pulse, relative to the holding current level. Similar to Kv1.5, the effects of all drugs were studied only when steady-state changes were achieved and data was analyzed as % block from control currents. IC$_{50}$ for rested state and use-dependent block was determined from the first and tenth pulses, respectively, during a series of 10 consecutive pulses delivered at 1 Hz. All experiments were performed at room temperature (22–24° C.).

C. Measurement of Use-Dependent and Rate-Dependent Block.

Use-dependent and rate-dependent block were assessed by measuring the currents elicited during trains of 150 msec long depolarizing pulses to a test potential of +40 mV from holding potentials of –80 mV and –50 mV in CHO cells and human atrial myocytes, respectively. Pulses were applied in 10 second long trains delivered after 30 second rest intervals at frequencies of 1 Hz (10 pulses) or 3 Hz (30 pulses). Percent block of the current is defined as the % decrease in the current amplitude produced by an agent during a given pulse relative to the control current amplitude for that pulse. Rested-state block is the block of the current during the first pulse in a train following the 30 sec rest period. Use-dependent block is block that occurs to a progessively greater extent with each successive depolarization in a train or sequence of pulses or depolarizations delivered at a given rate or frequency. Thus, during a train of 10 depolarizations at frequency of 1 Hz, use-dependent block is assessed as the ratio of the amount of block for the 10th pulse relative to block for the 1st pulse (rested state block) of the train. Rate-dependent block is block that occurs to a greater extent or preferentially at faster rates of depolarization or heart rates. Thus, rate-dependent block is assessed as the ratio of the amount of block of the current during the last pulse of the 10 sec train at 3 Hz vs. 1 Hz. Consequently, ratios of less than one (<1) are indicative of use-dependent and rate-dependent block and the lower the ratio the greater the degree of use and rate dependence.

D. Measurement of $I_{Ks}$ $I_{Kr}$ and $I_{K1}$ in Guinea Pig Ventricular Myocytes.

Cell preparation:

Guinea pig ventricular myocytes were isolated using a modification of the procedure described by Mitra et al., *Am. J. Physiol.* 249:H1056-60 (1985). Excised hearts were perfused through the aorta (retrograde fashion) at a rate of 10 ml/min with oxygenated, warmed (37° C.) solutions described below. The heart was initially perfused for 7 minutes with a Tyrode's solution containing, in mM: 132 NaCl, 4 KCl, 1.2 MgCl$_2$, 10 HEPES, 5 glucose, pH=7.2. The heart was then perfused with the same nominally Ca$^{2+}$-free solution containing 150 units/ml Type II collagenase (Worthington) and 0.5 units/ml Type XIV protease (Sigma) for 8 minutes. This perfusate was followed by a Tyrode's solution contianing 0.2 mM CaCl$_2$ (without enzymes) for 5 minutes. The digested ventricles were cut into small pieces and gently shaken until cells were visibly dispersed. The cells were stored at room temperature until use, within 8 hours after isolation.

Microelectrode fabrication:

The suction microelectrode technique described by Giles, W. R. and Shibata, E. F., "Voltage clamp of bull-frog cardiac pacemaker cells: a quantitative analysis of potassium currents", *J. Physiol.* 368:265–292 (1985) was used to voltage clamp the cells. Microelectrodes were made by using a two stage puller from square bore (1.0 mm o.d.) borosilicate capillary tubing. Pipettes were filled with 0.5 M K gluconate, 25 mM KCl and 5 mM K$_2$ATP. The electrodes had resistances of 3 to 7 Mohm when filled with this solution. After establishing whole-cell recording mode, negative pressure was maintained on the pipette using a 1 ml gas-tight syringe attached via air tight tubing to the suction port of the microelectrode holder. This minimized dialysis of the cell with the pipette solution.

Voltage-clamp technique:

To record K$^+$ currents, the cells were bathed in a Ca$^{2+}$-free Tyrode's solution containing 0.4 mM nisoldipine. Nisoldipine is a relatively specific blocker of L-type Ca$^{2+}$ channels, having no effect on K$^+$ currents at this concentration (Kass, R. S., "Nisoldipine: a new, more selective calcium current blocker in cardiac Purkinje fibers"., *J. Pharmacol. Exp. Ther.* 223:446–456, 1982). To record Ca$^{2+}$ currents, the cells were bathed in Tyrode's solution containing 1.8 mM Ca$^{2+}$ without nisoldipine. The cell chamber was superfused with solutions at a rate of 1–2 ml/minute, while maintaining the temperture at 35±120 C. A List EPC-7 clamp amplifier was used to voltage clamp the isolated cells. Series resistance was compensated 40–70%, and current was low-pass filtered at a cut-off frequency of 1 kHz. Data acquisition and analysis were performed using pClamp software (Axon Instruments, Burlingame, Calif.) and either an AST 386 or 486 computer. A variety of voltage pulse protocols were used to measure the three types of K$^+$ currents: inward rectifier ($I_{K1}$), rapidly activating delayed rectifier ($I_{Kr}$) and the slowly activating delayed rectifier ($I_{Ks}$). (Sanguinetti M. C. and Jurkiewicz, N. K., "Two components of cardiac delayed rectifier K$^+$ current: Differential sensitivity to block by Class III antiarrhythmic agents", *J. Gen Physiol* 1990; 96:194–214). Data was analyzed as % block from control membrane currents.

Solutions:

Nisoldipine was prepared as a 4 mM stock solution in polyethylne glycol 200. Compounds tested in this series were prepared as 10 mM stock solutions in dimethyl sulfoxide. At the final concentrations used, neither polyethylene glycol 200 nor dimethyl sulfoxide had any effect on any of the measured membrane currents.

Results:

As Table 1 indicates Compounds "A", "B", "C" and "D" provided use-dependent blockade of hKv1.5 in CHO cells and $I_{Kur}$ in human atrial myocytes. In addition, compounds "A", "B", and "C" are rate-dependent blockers of hKv1.5 in CHO cells. In human atrial myocytes, compound "A" was rate-dependent.

Table 1. Use- and Rate-Dependent blockers of hKv1.5 expressed in Chinese Hamster Ovary (CHO) cells and $I_{Kur}$ in human atrial myocytes. Compounds "A", "B", "C" and "D" are use-dependent and Compounds "A", "B", and "C" are rate-dependent as indicated by the use-dependent and rate-dependent ratios of <1 for block of hKv1.5 in CHO cells. Likewise in human atrial myocytes, all 4 compounds exhibited use-dependence and compound "A" was rate-dependent.

| Cpds | Conc. nM | Rested State 1st pulse @ 1 Hz | Use-Dpdnt 10th pulse @ 1 Hz | Rate-Dpdnt 30th pulse @ 3 Hz | Use-Dpdnt Ratio | Rate-Dpdnt Ratio | N |
|---|---|---|---|---|---|---|---|
| CHO cells - Average % Block ||||||||
| "A" | 30 | 21.2 | 38.5 | 57.5 | 0.55 | 0.67 | 4 |
|  | 100 | 32.1 | 64.6 | 82.9 | 0.50 | 0.78 | 4 |
| "B" | 100 | 23.3 | 29.6 | 44.9 | 0.79 | 0.66 | 4 |
|  | 300 | 43.5 | 56.6 | 67.5 | 0.77 | 0.84 | 3 |
| "C" | 30 | 6.6 | 15.7 | 38 | 0.42 | 0.41 | 6 |
|  | 100 | 51 | 75.5 | 91.1 | 0.68 | 0.83 | 6 |
| "D" | 100 | 31.1 | 34 |  | 0.91 |  | 3 |
|  | 300 | 52 | 62.5 |  | 0.83 |  | 3 |
| Human Atria - Average % Block ||||||||
| "A" | 30 | 21.9 | 33 | 48.4 | 0.66 | 0.68 | 3 |
|  | 100 | 35.6 | 59.7 | 75.7 | 0.60 | 0.79 | 4 |
| "B" | 100 | 10.4 | 17.8 | 11.6 | 0.58 | 1.53 | 6 |
|  | 300 | 25.8 | 31.3 | 33.8 | 0.82 | 0.93 | 9 |
| "C" | 30 | 35.7 | 43.2 | 42.9 | 0.83 | 1.01 | 3 |
|  | 100 | 63.8 | 67.9 | 60.1 | 0.94 | 1.13 | 3 |
| "D" | 100 | 61 | 68 |  | 0.90 |  | 4 |
|  | 1000 | 81.7 | 80 |  | 1.02 |  | 4 |

"N" represents the number of experiments for each compound at the specificied concentration.

Rested state block expressed as the % block relative to the control currents obtained under identical conditions was determined from the first pulse, whereas use-dependent % block was measured for the 10th pulse during a series of 10 consecutive pulses delivered at 1 Hz (10 sec train). Rate-dependent % block was determined from the 30th pulse during a series of 30 consecutive pulses delivered at 3 Hz (30 sec train). Use-dependent block is assessed as the ratio of the amount of block for the 10th pulse relative to block for the 1st pulse (rested state block) of the train at 1 Hz. Rate-dependent block is assessed as the ratio of the amount of block of the current during the last (30th vs. 10th, respectively) pulse of the 10 sec train at 3 Hz vs. 1 Hz. Currents were elicited by 150 ms depolarizing pulses to +40 mV from a holding potential of −80 mV (CHO cells) or −50 mV (Human atrium).

As Table 2 indicates, Compounds "A", "B", "C" and "D" provided selective blockade of hKv1.5 in CHO cells and $I_{Kur}$ in human atrial myocytes, yet blockade of the other cardiac K+ channels was minimal or absent.

Table 2. Selective blockers of hKv1.5 expressed in Chinese Hamster Ovary (CHO) cells and $I_{Kur}$ in human atrial myocytes relative to other cardiac K+ currents, $I_{K1}$, $I_{Kr}$ and $I_{Ks}$, measured in guinea pig ventricular myocytes as shown using Compounds "A", "B", "C" and "D".

| | Rested State IC$_{50}$ (nM) | | % Block (Guinea Pig Ventricle) | | |
|---|---|---|---|---|---|
| Compounds | CHO Cells Expressing hKv1.5 | $I_{Kur}$ in Human Atrium | $I_{K1}$ | $I_{Kr}$ | $I_{Ks}$ |
| "A" | 290 | 198 | 15% @ 3 µM | 3% @ 3 µM | 25% @ 3 µM |
| "B" | 278 | 780 | 15.1% @ 3 µM | 11.1% @ 3 µM | 12.2 @ 3 µM |
| "C" | 230 | 130 | 0% @ 3 µM | 8.4% @ 3 µM | 0% @ 3 µM |
| "D" | 120 | 80 | 4.4% @ 3 µM | 4.2% @ 3 µM | 13.6% @ 3 µM |

IC$_{50}$ for rested state block was determined from the first pulse during a series of 10 consecutive pulses delivered at 1 Hz. Currents were elicited by 150ms depolarizing pulses to +40 mV from a holding potential of −80 mV (CHO cells) or −50 mV (Human atrium).

Selectivity for block of cardiac K+ channels, $I_{K1}$, $I_{Kr}$, and $I_{Ks}$ was determined as previously described in guinea pig ventricular myocytes (U.S. Pat. No. 5,428,031).

In the novel method of treating or preventing arrhythmia of this invention, a suitable compound or pharmaceutically acceptable salt thereof, is administered in an amount ranging from about 0.1 to about 50 mg per kg of body weight per day, preferably from about 1.0 to about 30 mg per kg of body weight per day in a single dose or in 2 to 4 divided doses.

The compounds of this invention can be administered as the sole active ingredient or in combination with other antiarrhythmic agents or other cardiovascular agents. The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLES

The following examples illustrate the present invention without, however, limiting the same thereto.

Example 1

Synthesis of (2-Isopropyl-5-methylcyclohexyl)diphenylphosphine oxide (compound "A")

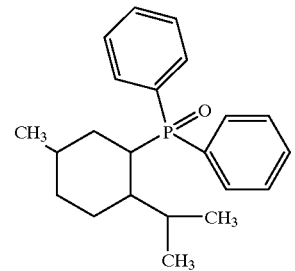

The synthesis of the title compound has been reported by J. D. Morrison and W. F. Masler in "Synthesis of methyl- and neomenthyldiphenyl-phosphine" (*J. Org. Chem.* (1974), 39(2), p 270–2), which is hereby incorporated by reference.

Example 2

Synthesis of 2-(Diphenylphosphinylmethyl)-4'-fluoro-3,5,3'-trimethylbiphenyl (compound "B")

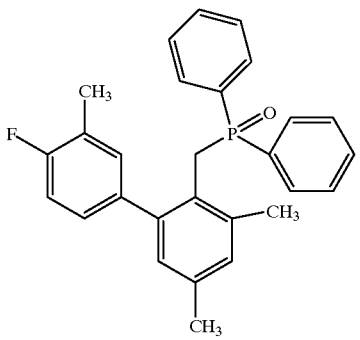

2.90 grams (12 mmol) of 2-(4-fluoro-3-methyl-phenyl)-4,6-dimethylbenzaldehyde (prepared according to Stokker, *Jour. Med. Chem.* Vol. 29 p.170, 1986) was reduced with 0.454 grams (12 mmol) of sodium borohydride in ethanol (20 mL) at 0° C. The reaction was stirred 1 hr, quenched with aqueous ammonium chloride and the mixture extracted with ether. The organic portion was dried (MgSO$_4$) and concentrated to give 2.90 grams of 2-(4-fluoro-3-methyl-phenyl)-4,6-dimethylbenzyl alcohol as an oil which solidified on standing. The crude solid was treated with 1.31 mL of thionyl chloride and heated on a steam bath for 1 hour. After cooling to room temperature, the crude mixture was taken up in water and extracted with ether. The ether was washed with water and dried(MgSO$_4$), and concentrated to give an oily residue which was purified by silica gel chromatography (25% methylene chloride/75% hexane) to give 2-(4-fluoro-3-methyl-phenyl)-4,6-dimethylbenzyl chloride as a solid.

2.06 grams (7.84 mmol) of 2-(4-fluoro-3-methyl-phenyl)-4,6-dimethylbenzyl chloride was treated with ethyldiphenylphosphinite (2.08 grams, 9.01 mmol) and heated to 150° C. for 3 hrs. After cooling to room temperature, the crude mixture was purified by silicagel chromatography ((10% acetone/90% methylene chloride) and the appropriate fractions concentrated and recrystallized from ether/hexane to provide the title compound (MP 109–111° C.).

Example 3

Synthesis of 6-(4-Chlorophenylthio)-2-(4-methoxyphenyl)-5-methyl-3-oxo-2,3-dihydropyridazine-4-carbonitrile (compound "C")

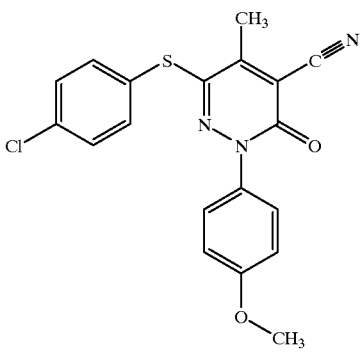

Preparation of 1-chloro-1-[(4-methoxyphenyl)hydrazonol]-2-propanone

A vigorously stirred suspension of 16.75 g(0.136 mole) of 4-methoxyaminobenzene in 960 ml of 1N hydrochloric acid was cooled to 0.5° C. and treated, dropwise, with 15.8 g of sodium nitrite dissolved in 200 ml of water. The temperature was maintained at 5° C.+/−1° C. during the addition. After addition was complete, the reaction mixture was stirred in the cold for an additional 30 min. The pH of the reaction mixture was adjusted to 4.5 with solid sodium acetate (72 g). The resultant mixture was treated, dropwise, with 24 g (0.178 mole) of 3-choro-2,4-pentanedione dissolved in 200 ml of methanol. After addition was complete, the reaction mixture was allowed to warm to room temperature over the next hour.

The suspension was extracted with 3–300 ml portions of ethyl ether. The combined extracts were washed with 4 volumes of water, dried over magnesium sulfate and filtered. The filtrate was evaporated in vacuo to yield 29 gm of a dark oil. The residue was dissolved in n-hexane:ethyl acetate (2:1) (approximately 400 ml) and the solution was passed over 1000 g of silica gel. Elution with n-hexane:ethyl acetate (3:1) yielded 1-chloro-1-[(4-methoxyphenyl) hydrazono]-2-propanone, mp 114–116° C. (hexane). $^1$H NMR(400 MHz, CDCl$_3$): 2.53 (s,3 H), 3.79 (s,3 H) 6.89 (d, J=9 Hz, 2 H), 7.24 (d, J=9 Hz, 2 H), 8.36 (broad s,1 H); PBBI-NH3/CI-MS Calculated for C$_{10}$H$_{11}$ClN$_2$O$_2$(226.6); found: 227 (M+1), 123

Preparation of 1-[(4-chlorophenyl)thio]-1-[(4-methoxyphenyl) hydrazono]-2-propanone A suspension of 31.7 g (0.139 mol) of 1-chloro-1-[(4-methoxyphenyl)hydrazono]-2-propanone in 400 ml of ethanol was treated with 23.4 g (0.161 mole) of 4-chlorothiophenol followed by 23.4 ml of triethylamine. The suspension was heated at reflux for 2 hours and cooled. The resultant suspension was filtered and the precipitate was washed with 1 portion of cold ethanol. The solids were dried in vacuo to yield 1-[(4-chlorophenyl)thio] -1-[(4-methoxyphenyl)hydrazonol-2-propanone, mp 111.5–113.5° C. $^1$H NMR(400 MHz, CDCl$_3$): 2.55 (s,3 H), 3.80(s,3 H), 6.88 (d, J=8 Hz, 2 H), 7.19 (d, J=8 Hz, 2 H), 7.13(m, 4 H), 9.2 (broad s,1 H) PBBI-NH$_3$/CI-MS Calculated for C$_{16}$H$_{15}$ClN$_2$SO$_2$(334.8); found: 335 (M+1), 234, 124

Preparation of 6-[(4-chlorophenyl)thio]-2,3-dihydro-2-(4-methoxyphenyl)-5-methyl-3-oxo-4-pyridazinecarbonitrile A flasked equipped with a claisen distillation head and magnetic stirring was charged with an intimate mixture of 32.6 g (0.097 mole) 1-[(4-chlorophenyl)thio]-1-1(4-methoxyphenyl) hydrazono]-2-propanone, 24.8 ml of ethylcyanoacetate and 12.2 g of ammonium acetate. The mixture was heated under a nitrogen atmosphere at 160° C. for 30 min. The reaction mixture was cooled and dissolved in methylene chloride. The organic layer was washed successively with saturated aqueous sodium bicarbonate and water. The organic layer was dried over magnesium sulfate and evaporated in vacuo to yield semi pure product. The residue was recrystallized from 1900 ml of ethanol to yield 6-[(4-chlorophenyl)thio]-2,3-dihydro-2-(4-methoxyphenyl)-5-methyl-3-oxo-4-pyridazinecarbonitrile, mp 146–148° C. (EtOH). $^1$H NMR(400 MHz, CDCl$_3$) 2.15 (s, 3 H),2.53 (s, 3 H), 6.84 (d, J=9.2 Hz, 2 H), 7.33 (d, J=9.2 Hz, 2 H), 7.35 (d, J=8.6 Hz, 2 H), 7.40 (d, J=8.6 Hz, 2 H). PBBI-NH3/Cl-MS Calculated for $C_{19}H_{14}ClN_3O_2S$ (383.8); Found 383 (M+1)

Example 4
Synthesis of 2-(4-methylphenyl)-5-methyl-3-oxo-6-(4-methyl-phenylthio)-2,3-dihydropyridazine-4-carbonitrile (compound "D")

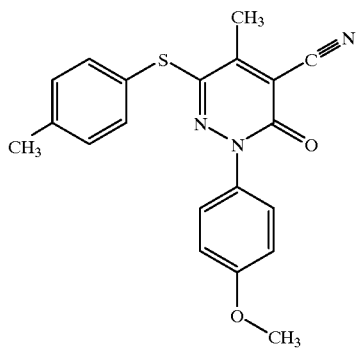

Preparation of 1-chloro-1-r(4-methoxyphenyl)hydrazonol-2-propanone

A vigorously stirred suspension of 16.75 g(0.136 mole) of 4-methoxyaminobenzene in 960 ml of IN hydrochloric acid was cooled to 5° C. and treated, dropwise, with 15.8 g of sodium nitrite dissolved in 200 ml of water. The temperature was maintained at 5° C.+/−1° C. during the addition. After addition was complete, the reaction mixture was stirred in the cold for an additional 30 min. The pH of the reaction mixture was adjusted to 4.5 with solid sodium acetate (72 g). The resultant mixture was treated, dropwise, with 24 g (0.178 mole) of 3-chloro-2,4-pentanedione dissolved in 200 ml of methanol. After addition was complete, the reaction mixture was allowed to warm to room temperature over the next hour.

The suspension was extracted with 3–300 ml portions of ethyl ether. The combined extracts were washed with 4 volumes of water, dried over magnesium sulfate and filtered. The filtrate was evaporated in vacuo to yield 29 gm of a dark oil. The residue was dissolved in n-hexane:ethyl acetate (2:1) (approximately 400 ml) and the solution was passed over 1000 g of silica gel. Elution with n-hexane: ethyl acetate (3:1) yielded 1-chloro-1-[(4-methoxyphenyl) hydrazono]-2-propanone, mp 114–116° C. (hexane). $^1$H NMR(400 MHz, CDCl$_3$): 2.53 (s,3 H), 3.79 (s,3 H) 6.89 (d, J=9 Hz, 2 H), 7.24 (d, J=9 Hz, 2 H), 8.36 (broad s,1 H); PBBI-NH3/Cl-MS Calculated for $C_{10}H_{11}ClN_2O_2$(226.6); found: 227 (M+1), 123.

A more preferred process for the production of 1-chloro-1-[(4-methoxyphenyl)hydrazono]-2-propanone is as follows. A vigorously stirred suspension of 49.2 g (0.339 mole) of 4-methoxy-aminobenzene in 400 ml of 5N hydrochloric acid was cooled to 0° C. and treated, dropwise, with 30.4 g (0.440 mol) of sodium nitrite dissolved in 100 ml of water. The temperature was maintained at 0–5° C.+/−1° C. during the addition. After addition was complete, the reaction mixture was stirred at 0° C.+/−1° for an additional 30 min.

The cold solution was poured slowly into a vigorously stirred solution of 54 g (0.401 mol) of 3-chloro-2,4-pentanedione dissolved in 280 ml of pyridine and 280 ml of water pre-cooled to −8° C.+/−1° C. The ice bath was removed and the resultant yellow suspension was stirred at 5° C.+/−1° C. for 30 minutes, diluted with 500 ml of water. The yellow solids were collected by filtration and washed with 300 ml water (4 times). The wet crude product was dissolved in 500 ml of methylene chloride. The organic layer was dried over magnesium sulfate, filtered and evaporated in vacuo to yield 56.45 g of 1-chloro-1-[(4-methoxy-phenyl) hydrazono]-2-propanone. The purity of the product was sufficient for further utilization. Further purification was accomplished by chromatography over silica gel and elution with elution with n-hexane:ethyl acetate (3:1) to yield 1-chloro-1-[(4-methoxyphenyl)hydrazono]-2-propanone, mp 114–116° C. (hexane). $^1$H NMR(400 MHz, CDCl$_3$): 2.53 (s,3 H), 3.79 (s,3 H) 6.89 (d, J=9 Hz, 2 H), 7.24 (d, J=9 Hz, 2 H), 8.36 (broad s,1 H); PBBI-NH3/Cl-MS Calculated for $C_{10}H_{11}ClN_2O_2$(226.6); found: 227 (M+1), 123

Preparation of 1-[(4-methylphenyl)thio]-1-[(4-methoxyphenyl)-hydrazono]-2-propanone A suspension of 31.7 g (0.139 mol)of 1-chloro-1-[(4-methoxyphenyl)hydrazono]-2-propanone in 400 ml of ethanol was treated with 23.4 g of 4-methylthiothiophenol and 23.4 of triethylamine. The suspension was heated at reflux for 2 hours and cooled. The resultant suspension was filtered and the precipitate was washed with 1 portion of cold ethanol. The solids were dried in vacuo to yield 1-[(4-methylthiophenyl)thio]-1-[(4-methoxyphenyl)hydrazono]-2-propanone, mp 124–127° C. $^1$H NMR(400 MHz, CDCl$_3$): 2.41 (s, 3 H), 2.54 (s, 3 H), 3.78 (s, 3 H), 6.87 (d, J=8.8 Hz, 2 H), 7.12 (m, 6 H), 9.20 (broad s, 1 H).

Preparation of 6-[(4-methylphenyl)thio]-2,3-dihydro-2-(4-methoxy-phenyl)-5-methyl-3-oxo-4-pyridazinecarbonitrile An intimate, magnetically stirred mixture of 440 mg (1.40 mmol) of 1-[(4-methylphenyl)thio]-1-[(4-methoxyphenyl) hydrazono]-2-propanone 370 μl of ethylcyanoacetate and 178 mg of ammonium acetate was heated under a nitrogen atmosphere at 160° C. for 30 min. The reaction mixture was cooled and dissolved in methylene chloride. The organic layer was washed successively with saturated aqueous sodium bicarbonate and water. The organic layer was dried over magnesium sulfate and evaporated in vacuo to yield semi-pure product. The residue was recrystallized from ethanol to yield 6-[(4-methylphenyl)thio]-2,3-dihydro-2-(4-methoxyphenyl)-5-methyl-3-oxo-4-pyridazinecarbonitrile, mp 148–149° C.(EtOH). 1H NMR(400 MHz, CDCl$_3$) 2.35 (s, 3 H), 2.52 (s, 3 H), 3.78 (s, 3 H), 6.82 (d, J=9.2 Hz, 2 H), 7.18 (d, J=8 Hz, 2 H), 7.34 (d, J=8 Hz, 2 H), 7.36 (d, J=9.2 Hz, 2 H).

Example 5
In Vivo Cardiac Electrophysiologic and Antiarrhythmic Effects of Compound "A" in Anesthetized Dog Effects on heart rate, mean arterial pressure, electrocardiographic intervals and atrial, atrioventricular (AV) nodal and ventricular electrophysiologic parameters can be assessed in chloralose-anesthetized dogs. Bipolar epicardial electrodes can be sutured onto the left atrium, right atrium and left ventricle for electrical pacing and for the introduction of extrastimuli for the measurement of atrial, ventricular and atrioventricular (AV) nodal excitation thresholds and refractory periods. The following indices of cardiac conduction and refractoriness can be determined before and after the cumulative intravenous administration of test agent at a pacing frequency of 2.5 Hz (CL 400 msec): atrial and ventricular excitation thresholds (AET and VET, respectively); atrial relative (ARRP, 2x AET) and effective (AERP, 10x AET) refractory periods; ventricular relative (VRRP, 2x VET) and effective (VERP, 10x VET) refractory periods; AH interval, an index of AV nodal conduction; HV interval, an index of His-ventricular conduction time; P-A interval, an index of intraatrial conduction; and H-EG interval, an index of ventricular conduction; and paced ECG QT interval. AV nodal functional refractory period (AVNFRP) and SA conduction time (SACT) can be determined by the introduction of atrial extrastimuli during sinus rhythm, and the monitoring of ventricular response. Electrocardiographic intervals can be determined during sinus rhythm; the rate-corrected ECG QTc interval was calculated as: QTc=QT (msec)/√R—R (see). Test agent can be administered as cumulative i.v. doses of 1, 3 and 10 mg/kg, with each dose administered over a period of 15 min in a vehicle of PEG-200. Hemodynamic, electrocardiographic and cardiac electrophysiologic determinations can be made immediately following the infusion of each dose.

Example 6
Termination of Atrial Flutter in Anesthetized Dog

The potential of a test compound to terminate ongoing atrial arrhythmia can be assessed in a pentobarbital-anesthetized canine model of atrial flutter. In this model, atrial flutter can be induced following a Y-shaped surgical lesion comprised of an intercaval incision and a connecting incision across the right atrium. Bipolar epicardial electrodes can be placed on the inferior vena cava and right atrium for atrial pacing and for recording local atrial activation. Sustained atrial flutter can be initiated in dogs by electrical burst pacing (14–20 Hz) of the atria. Atrial cycle lengths of the atrial arrhythmias have been shown to range from 105–182 msec (i.e. approx 330–570 atrial cycles/min). Intravenous bolus administration of PEG-200 vehicle alone has been shown to have no effect on the ongoing atrial arrhythmia in all three animals.

Example 7
Determination of Use-dependent Block for Compound "A"

Kv1.5 and $I_{Kur}$ were elicited by trains of 10 depolarizing voltage steps delivered at a frequency of 1 Hz. Use-dependence was assessed by comparing the degree of block during the first and last (10th) pulse of the train, respectively of (2-isopropyl-5-methylcyclohexyl) diphenyl-phosphine oxide blocked Kv1.5 in CHO cells with $IC_{50}$ values of 290 nM and 73 nM for the first and last pulse, respectively. Similar results were obtained with $I_{Kur}$. For example, $I_{Kur}$ measured in human atrial myocytes was blocked by of (2-isopropyl-5-methylcyclohexyl)diphenyl-phosphine oxide with $IC_{50}$ values of 198 nM and 70 nM for the first and last pulse. These results demonstrate a strong use-dependent profile and suggest that this method may provide greater blockade at atrial rates typically encountered during atrial flutter and/or fibrillation, for example 350 to 600 beats/min. These results also show that repetitive depolarization or use-dependence can strongly influence the estimated potency of a compound. Because this method of treatment potentially provides better blockade at faster heart rates, efficacy and tolerability by the patient are expected to be greater.

Example 8
Determination of Rate-Dependent Block for Compound "A"

Kv1.5 and $I_{Kur}$ were elicited by trains of 150 msec long depolarizing pulses to a test potential of +40 mV from holding potentials of −80 mV and −50 mV in CHO cells and human atrial myocytes, respectively. Pulses were applied in 10 second long trains delivered after 30 second rest intervals at frequencies of 1 Hz (10 pulses) or 3 Hz (30 pulses). Percent (%) block of the current is defined as the % decrease in the time-dependent current amplitude at the end of the test pulse produced by an agent during a given pulse relative to the control current amplitude for that pulse. Rate-dependent block is block that occurs to a greater extent or preferentially at faster rates of depolarization or heart rates. Thus, rate-dependent block is assessed as the ratio of the amount of block of the current during the last pulse of 10 second trains at 3(30th pulse) Hz vs. 1 Hz (10th pulse). A ratio of less than one (<1) is indicative of rate-dependent block and the lower the ratio the greater the degree of rate dependence. Compound "A" (2-isopropyl-5-methylcyclohexyl) diphenyl-phosphine oxide at a concentration of 30 nM blocked Kv1.5 in CHO cells by an average of 38.5% and 57.5% at 1 and 3 Hz, respectively, to yield a rate dependence ratio of 0.67, indicating that the degree of block was greater at 3 Hz than at 1 Hz and was therefore rate-dependent. Likewise, Compound "A" (2-isopropyl-5-methylcyclohexyl) diphenyl-phosphine oxide at a concentration of 100 nM blocked Kv1.5 in CHO cells by an average of 64.6% and 82.9% at 1 and 3 Hz, respectively to yield a rate dependence ratio of 0.78, indicating that the rate dependence was manifest at varying concentrations of the compound. Similar results were obtained with $I_{Kur}$ measured in human atrial myocytes. For example, Compound "A" (2-isopropyl-5-methylcyclohexyl) diphenyl-phosphine oxide at a concentration of 30 nM blocked $I_{Kur}$ in human atrial myocytes by an average of 33% and 48.4% at 1 and 3 Hz, respectively to yield a rate dependence ratio of 0.68, whereas at a concentration of 100 nM it blocked IKur by 59.7% and 75.7% at 1 and 3 Hz, respectively to yield a rate dependence ratio of 0.79. These results demonstrate a strong rate-dependent profile and suggest that this method may provide greater blockade at atrial rates typically encountered during flutter and/or atrial fibrillation, for example 350 to 600 beats/min. These results also show that stimulus rate can strongly influence the estimated potency of a compound. Because this method of treatment provides better blockade at faster heart rates, efficacy and tolerability by the patient are expected to be greater.

What is claimed is:

1. A method of treating or preventing cardiac arrhythmia in mammals comprising the administration of a therapeutically effective amount of a phosphine oxide compound which provides for use-dependent and/or rate-dependent block of the ultra-rapidly-activating delayed rectifier K$^+$ current ($I_{Kur}$) at a concentration of about 1 µM or less.

2. The method according to claim 1, wherein the concentration which blocks $I_{Kur}$ by 50% ($IC_{50}$) is at least about 10 fold lower than the concentration which blocks a slowly activating delayed rectifier potassium K$^+$ current ($I_{Ks}$), a rapidly activating and deactivating delayed rectifier potassium current ($I_{Kr}$) or an inward rectifier K+ current, $I_{K1}$.

3. The method according to claim 2, wherein the compound administered is a phosphine oxide compound or its pharmaceutically acceptable salt, hydrate or crystal form.

4. The method according to claim 3, wherein the phosphine oxide compound administered is illustrated by Formula II:

wherein
$R^{1a}$ is phenyl;
$R^{2a}$ is aryl;
$R^{3a}$ is selected from:
  a) $C_1$–$C_6$ alkyl-aryl, where the aryl group may be unsubstituted or substituted with one to four substituents independently selected from halo and $C_1$–$C_3$ alkyl; and
  b) unsubstituted or substituted benzyl, where the substituent is ($C_1$–$C_5$ alkyl)n;
n is selected from 0, 1, 2, 3 and 4;
or a pharmaceutically acceptable salt, hydrate or crystal form thereof.

5. The method according to claim 3, wherein the compound administered is selected from the group consisting of:
(2-Isopropyl-5-methylcyclohexyl)diphenylphosphine oxide;
2-(Diphenylphosphinylmethyl)-4'-fluoro-3,5,3'-trimethyl-biphenyl;
or a pharmaceutically acceptable salt, hydrate or crystal form thereof.

6. A method of treating or preventing supraventricular tachyarrhythmia comprising the administration of a therapeutically effective amount of a phosphine oxide compound which provides for use-dependent and/or rate-dependent block of the ultra-rapidly-activating delayed rectifier $K^+$ current ($I_{Kur}$) at a concentration of about 1 μM or less.

7. The method according to claim 6, wherein the concentration which blocks $I_{Kur}$ by 50% ($IC_{50}$) is at least about 10 fold lower than the concentration which blocks a slowly activating delayed rectifier potassium $K^+$ current ($I_{Ks}$), a rapidly activating and deactivating delayed rectifier potassium current ($I_{Kr}$) or an inward rectifier K+ current, $I_{K1}$.

8. The method according to claim 6, wherein the compound administered is a phospine oxide compound or its pharmaceutically acceptable salt, hydrate or crystal form.

9. The method according to claim 8, wherein the phosphine oxide compound administered is illustrated by Formula II:

wherein
$R^{1a}$ is phenyl;
$R^{2a}$ is aryl;
$R^{3a}$ is selected from:
  a) $C_1$–$C_6$ alkyl-aryl, where the aryl group may be unsubstituted or substituted with one to four substituents independently selected from halo and $C_1$–$C_3$ alkyl; and
  b) unsubstituted or substituted benzyl, where the substituent is ($C_1$–$C_5$ alkyl)n;
n is selected from 0, 1, 2, 3 and 4;
or a pharmaceutically acceptable salt, hydrate or crystal form thereof.

10. The method of claim 8, wherein the compound administered is selected from the group consisting of:
(2-Isopropyl-5-methylcyclohexyl)diphenylphosphine oxide;
2-(Diphenylphosphinylmethyl)-4'-fluoro-3,5,3'-trimethyl-biphenyl;
or a pharmaceutically acceptable salt, hydrate or crystal form thereof.

11. A method for treating and/or preventing atrial arrhythmia comprising the administration of a therapeutically effective amount of a phosphine oxide compound which provides for use-dependent and/or rate-dependent block of the ultra-rapidly-activating delayed rectifier $K^+$ current ($I_{Kur}$) at a concentration of about 1 μM or less.

12. The method according to claim 11, wherein the concentration which blocks $I_{Kur}$ by 50% ($IC_{50}$) is at least about 10 fold lower than the concentration which blocks a slowly activating delayed rectifier potassium $K^+$ current ($I_{Ks}$), a rapidly activating delayed rectifier potassium current ($I_{Kr}$) or an inward rectifier K+ current, $I_{K1}$.

13. The method according to claim 12, wherein the compound administered is a phosphine oxide compound.

14. The method according to claim 13, wherein the phosphine oxide compound administered is illustrated by Formula II:

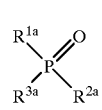

wherein
$R^{1a}$ is phenyl;
$R^{2a}$ is aryl;
$R^{3a}$ is selected from:
  a) $C_1$–$C_6$ alkyl-aryl, where the aryl group may be unsubstituted or substituted with one to four substituents independently selected from halo and $C_1$–$C_3$ alkyl; and
  b) unsubstituted or substituted benzyl, where the substituent is ($C_1$–$C_5$ alkyl)n;
n is selected from 0, 1, 2, 3 and 4;
or a pharmaceutically acceptable salt, hydrate or crystal form thereof.

15. The method according to claim 13, wherein the compound administered is selected from the group consisting of:
(2-Isopropyl-5-methylcyclohexyl)diphenylphosphine oxide;
2-(Diphenylphosphinylmethyl)-4'-fluoro-3,5,3'-trimethyl-biphenyl;
or a pharmaceutically acceptable salt, hydrate or crystal form thereof.

16. A method of treating and/or preventing atrial flutter or atrial fibrillation comprising the administration of a therapeutically effective amount of a phosphine oxide compound which provides for use-dependent and/or rate-dependent block of the ultra-rapidly-activating delayed rectifier $K^+$ current ($I_{Kur}$) at a concentration of about 1 μM or less.

17. The method according to claim 16, wherein the concentration which blocks $I_{Kur}$ by 50% ($IC_{50}$) is at least about 10 fold lower than the concentration which blocks a slowly activating delayed rectifier potassium $K^+$ current ($I_{Ks}$), a rapidly activating and deactivating delayed rectifier potassium current ($I_{Kr}$) or an inward rectifier $K^+$ current, $I_{K1}$.

18. The method according to claim 17, wherein the compound administered is a phosphine oxide compound.

19. The method according to claim 18, wherein the phosphine oxide compound administered is illustrated by Formula II:

II wherein
$R^{1a}$ is phenyl;
$R^{2a}$ is aryl;
$R^{3a}$ is selected from:
a) $C_1$–$C_6$ alkyl-aryl, where the aryl group may be unsubstituted or substituted with one to four substituents independently selected from halo and $C_1$–$C_3$ alkyl; and
b) unsubstituted or substituted benzyl, where the substituent is $(C_1$–$C_5$ alkyl)n;

n is selected from 0, 1, 2, 3 and 4;
or a pharmaceutically acceptable salt, hydrate or crystal form thereof.

20. The method according to claim 18, wherein the compound administered is selected from the group consisting of:

(2-Isopropyl-5-methylcyclohexyl)diphenylphosphine oxide;

2-(Diphenylphosphinylmethyl)-4'-fluoro-3,5,3'-trimethyl-biphenyl;

or a pharmaceutically acceptable salt, hydrate or crystal form thereof.

21. A method of treating or preventing atrial fibrillation comprising the administration of a therapeutically effective amount of a phosphine oxide compound which provides for use-dependent and/or rate-dependent block of the ultra-rapidly-activating delayed rectifier K$^+$ current ($I_{Kur}$) at a concentration of about 1 μM or less.

22. The method according to claim 21, wherein the concentration which blocks $I_{Kur}$ by 50% ($IC_{50}$) is at least about 10 fold lower then the concentration which blocks a slowly activating delayed rectifier potassium K$^+$ current ($I_{Ks}$), a rapidly activating and deactivating delayed rectifier potassium current ($I_{Kr}$) or an inward rectifier K+ current, $I_{K1}$.

23. The method according to claim 22, wherein the compound administered is a phosphine oxide compound.

24. The method according to claim 23, wherein the phosphine oxide compound administered is illustrated by Formula II:

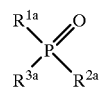

II wherein
$R^{1a}$ is phenyl;
$R^{2a}$ is aryl;
$R^{3a}$ is selected from:
a) $C_1$–$C_6$ alkyl-aryl, where the aryl group may be unsubstituted or substituted with one to four substituents independently selected from halo and $C_1$–$C_3$ alkyl; and
b) unsubstituted or substituted benzyl, where the substituent is $(C_1$–$C_5$ alkyl)n;

n is selected from 0, 1, 2, 3 and 4;
or a pharmaceutically acceptable salt, hydrate or crystal form thereof.

25. The method according to claim 23, wherein the compound administered is selected from the group consisting of:

(2-Isopropyl-5-methylcyclohexyl)diphenylphosphine oxide;

2-(Diphenylphosphinylmethyl)-4'-fluoro-3,5,3'-trimethyl-biphenyl;

or a pharmaceutically acceptable salt, hydrate or crystal form thereof.

* * * * *